(12) United States Patent
Wilkinson

(10) Patent No.: US 6,511,323 B1
(45) Date of Patent: Jan. 28, 2003

(54) TOOTH PREPARATION INSTRUMENT AND SYSTEM OF ITS USE

(76) Inventor: Alfred Harper Ben Wilkinson, 5759 Brentwood Trace, Brentwood, TN (US) 37027

( * ) Notice: Subject to any disclaimer, the term of this patent is extended or adjusted under 35 U.S.C. 154(b) by 0 days.

(21) Appl. No.: 09/976,214

(22) Filed: Oct. 15, 2001

(51) Int. Cl.[7] .................................................. A61C 5/10
(52) U.S. Cl. ........................ 433/223; 433/165; 433/29; 433/72; 433/51
(58) Field of Search .............................. 433/72, 75, 76, 433/51, 165, 218, 219, 223, 213, 29

(56) References Cited

U.S. PATENT DOCUMENTS

| | | | | |
|---|---|---|---|---|
| 3,445,935 A | * | 5/1969 | Marshall | 433/51 |
| 3,508,334 A | * | 4/1970 | Weissman | 433/76 |
| 3,838,517 A | * | 10/1974 | Michnick | 433/72 |
| 3,979,829 A | | 9/1976 | Lemos | |
| 4,144,645 A | | 3/1979 | Marshall | |
| 4,353,696 A | | 10/1982 | Bridges | 433/125 |
| 4,473,354 A | * | 9/1984 | Rigaud | 433/218 |
| 4,526,542 A | * | 7/1985 | Kochis | 433/165 |
| 4,941,826 A | | 7/1990 | Loran et al. | 433/51 |
| 5,545,039 A | | 8/1996 | Mushabac | 433/215 |
| 5,575,656 A | | 11/1996 | Hajjar | 433/219 |
| 5,941,706 A | * | 8/1999 | Ura | 433/165 |

* cited by examiner

*Primary Examiner*—Cary E. O'Connor
(74) *Attorney, Agent, or Firm*—Jacobson Holman PLLC

(57) ABSTRACT

At an initial office visit, the dentist makes an impression of the portion of the mouth in which the tooth is located, with upper and lower occusal surfaces at or below the gum line. After preparation of a crown, the dentist presses the surface contour tool against the biting surface of the tooth to determine the depth settings for at least one burr in a surface tool that will remove the upper surface of the tooth and create a working surface for the material removal device. The dentist inserts at least one burr with the proper length in this tool so that when the tool is lowered onto the tooth, a flat surface will be created. The flat surface tool and the center hole drilling burr are operated with a device that locks onto the tooth and ensures that the top surface of the tooth will be perpendicular to the central line of the tooth. The dentist inserts the guide pin of the material removal device in the center hole and begins to remove material from the side of the tooth.

24 Claims, 4 Drawing Sheets

TOOTH PREPARATION INSTRUMENT AND SYSTEM OF ITS USE

FIELD OF THE INVENTION

The present invention consists of a tooth preparation instrument and system that creates a tapered conical shape from a tooth, with pre-determined dimensions, making it possible for a lab technician to independently and simultaneously create a crown that exactly fits the prepared tooth. The crown is ready for permanent placement on the prepared tooth at the time of preparing the tooth. Use of the invention saves considerable time and effort as compared with current methods.

BACKGROUND OF THE INVENTION

Currently, a tooth is prepared for a crown in the following manner. First, during an initial office visit, the dentist makes an impression of the portion of the mouth in which the tooth is located, with upper and lower occusal surfaces. From this impression a lab technician will later create a stone study model.

The dentist then removes tooth material with a high-speed drill, relying on eyesight and expertise to create a form on which a crown will be cemented. This form begins with a narrow shoulder at the gum line and tapers inward as it rises to a flattened top that ends just below the lowest level of the tooth's original biting surface.

The dentist then makes an impression of the prepared tooth and sends it to the lab technician along with the tooth impression, prepared prior to removal of tooth material. The dentist makes and installs a temporary crown for the prepared tooth.

Using the impression of the prepared tooth, the lab technician produces a crown that matches the dentist's color and material specifications and sends it to the dentist. At the patient's second visit, the dentist tests and adjusts the crown as necessary before cementing it in place.

SUMMARY OF THE INVENTION

By the present invention, the following steps will be performed. At an initial office visit, the dentist makes an impression of the portion of the mouth in which the tooth is located, with upper and lower occusal surfaces. From this impression the lab technician will later create a stone study model.

The dentist, at a second office visit or, in a preferred embodiment, during the same office visit when a lab technician is available in the office for simultaneous creation of the crown, presses a surface contour tool against the biting surface of the tooth to determine the depth settings for at least one burr in a surface tool that will remove the upper surface of the tooth and create a working surface for the material removal device.

The dentist inserts at least one burr with the proper length in this tool so that when the tool is lowered onto the tooth, a flat surface will be created. It is essential that this surface be aligned perpendicular to the center line of the tooth. The dentist also calculates the center of the tooth and sets the depth of the burr that will drill the center hole for guiding the material removal device.

The flat surface tool and the center hole drilling burr are operated with a device that locks onto the tooth and ensures that the top surface of the tooth will be perpendicular to the central line of the tooth. The dentist makes two calculations. First, the distance in 0.1 mm increments between a predetermined point below the lowest level on the tooth's biting surface (beginning level) and the gum line (ending level). This will be the height of the prepared tooth. The second calculation is the distance from the center of the tooth's biting surface to a predetermined point inside the narrowest part of the tooth at the gum line (the shoulder). This will be the radius at the shoulder of the prepared tooth. The dentist inserts tapered burrs of predetermined lengths and a guide pin of the required length into the material removal device and feeds the calculations into a computer processor which will control the material removal device. A print out of the calculations is forwarded to the technician for confirmation of the requirements for the prepared crown or a bridge.

To initiate operation of the material removal device, a center hole is drilled. A flat surface tool is used to remove tooth material, smoothing the surface as necessary. The dentist inserts the guide pin of the material removal device in the center hole and begins to remove material from the side of the tooth. Each cycle around the tooth removes 0.1–0.5 mm. The various burrs are tapered and may be diamond burrs to create the required chamfer on the sides of the tooth.

The device has four computer controlled lights to guide the dentist. A green light indicates that the device is level with the top surface. A blue light is activated when a desired depth is achieved as also limited by the length of the burr. Two lights (one red and one yellow) warn the dentist that the device is tilted so that it is creating an undercut (red) or drilling too far toward the outer edge of the shoulder (yellow).

After each cycle, the dentist moves the depth setting another 0.1–0.5 mm until the required depth is reached. The burrs on the device, ranging in number from one to six, are preset so that they cannot be extended beyond the depth that has been calculated by the dentist.

While the dentist has been removing tooth material the lab technician has independently and simultaneously, if the technician is immediately available produced a crown or bridge that will fit the prepared tooth. The prepared crown will have the same internal dimensions as the prepared tooth and also the same characteristics (color, shape) as the original tooth.

Some of the advantages of the invention are that a dentist can prepare a tooth knowing that the crown will fit precisely, because the prepared tooth will have the same exterior dimensions as the interior opening on the crown so that the crown will precisely fit the prepared tooth. In addition, only one office visit is necessary to prepare the tooth and install a permanent crown. A patient will not require a temporary crown. The dentist will not have to make an impression of the prepared tooth and wait for the technician to produce the crown.

Alternatively, a series of pre-prepared crowns of various shapes and colors may be available to the dentist. Since the tooth will be prepared to a predetermined truncated cone size, pre-formed crowns having a similar pre-formed internal truncated conical recess may be available to the dentist. This would insure immediate accurate crown installation during a single office visit.

Accordingly, it is an object of the present invention to provide a tooth preparation instrument and system of its use including preparing an impression of a portion of a mouth in which a diseased tooth is located and simultaneously preparing or using a pre-formed permanent crown during the same office visit during which the impression was made with the crown having a predetermined internal recess calculated to exactly match a predetermined prepared tooth size so that the crown may be permanently secured to the prepared tooth during a single office visit.

It is another object of the present invention to prepare a tooth based upon a predetermined internal recess of the crown so that the internal recess of the crown will match the prepared tooth for permanently securing the crown during a single office visit.

It is yet another object of the present invention to control the preparation of a tooth for receipt of a crown so that the external dimensions of the prepared tooth coincide with the internal dimensions of the crown and the exterior surface of the crown matches the original shape of the tooth prior to preparation, including taking an impression of the tooth, preparing the crown and installing the crown during a single office visit.

These and other objects of the invention, as well as many of the intended advantages thereof, will become more readily apparent when reference is made to the following description taken in conjunction with the accompanying drawings.

DETAILED DESCRIPTION OF THE PREFERRED EMBODIMENTS

Figure 1:
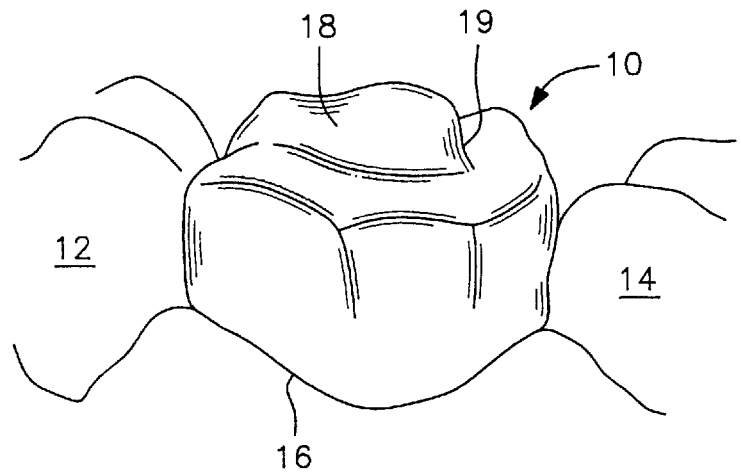
FIG. 1 is a perspective view of a tooth to be treated by the method, apparatus and system of the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

With reference to the drawings, in general and to FIGS. 1 through 5, in particular, the method, apparatus and system embodying the teachings of the subject invention is shown. With reference to FIG. 1, a tooth 10 is shown located between two adjacent teeth 12 and 14, extending below a gum line 16.

Figure 2:
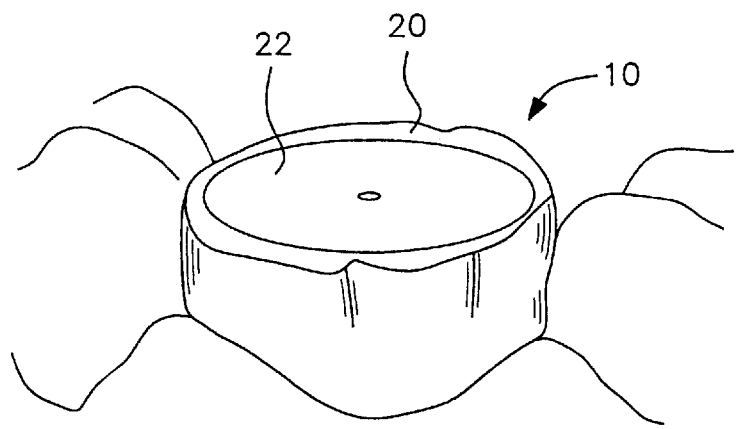
FIG. 2 is a perspective view of a tooth having a flat surface ground on the top of the tooth and a round pattern disk being placed on top of the flat surface.

In FIG. 2, after an impression has been made of the tooth, the tooth 10 has had its upper surface 18 ground into a flat surface 20 which is approximately at a depth of the lowest indentation 19 projecting downwardly from the upper surface 18 in the pretreated tooth 10. The flat surface 20 will provide a reference plane for further treatment of the tooth 10 by attaching a crown to the tooth.

A perfectly round pattern disk 22 of paper, plastic or other disposable material of an appropriate size for each tooth so as to form a complete circle within the confines of all lateral edges of the flat surface 20 of the tooth is selected and placed on top of the flat surface 20 of the tooth 10. A bottom surface of the disk.22 includes an adhesive to maintain the positioning of the disk 22.

Figure 3:
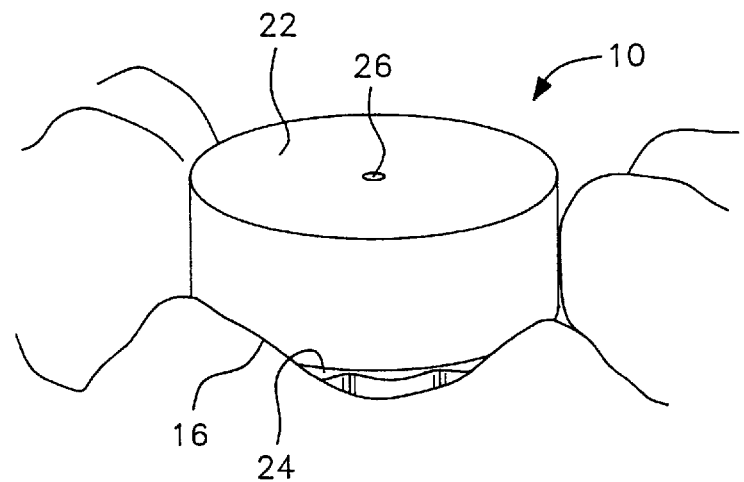
FIG. 3 is a perspective view of a tooth having an upper portion ground into a cylindrical configuration approximating the diameter of the disk placed on top of the tooth as shown in FIG. 2.

The pattern disk 22 is used as a guide to grind the sides of a tooth 10 to a nearly perfect cylindrical shape as shown in FIG. 3. A shoulder 24 of the tooth is maintained at the bottom of the cylindrically shaped portion, adjacent to the gum line 16. At the flat surface 20 of the tooth is drilled a hole 26 of an approximate depth of ⅛ of an inch and having a diameter of approximately 1/32 of an inch.

Figure 4:
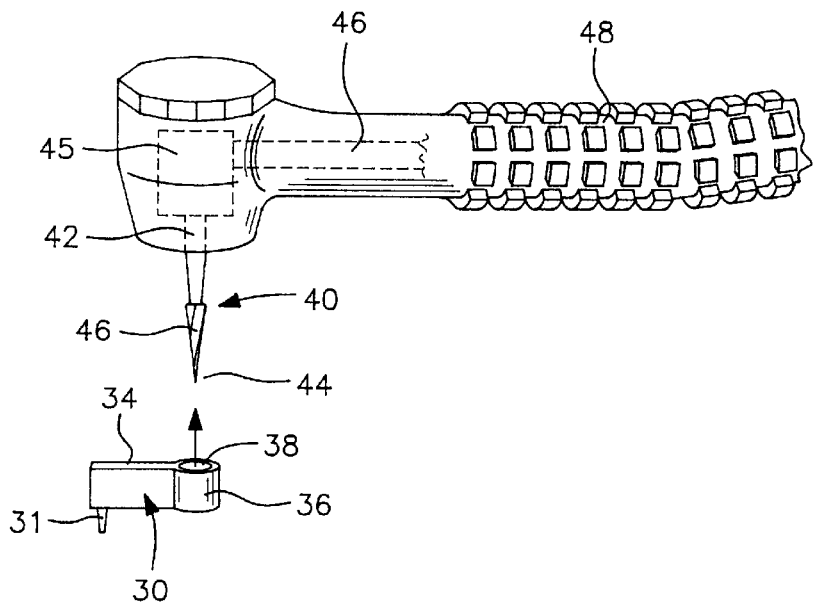
FIG. 4 is an exploded view of a compass grinder and a drill bit located in a hand piece providing a rotating force to the drill bit.

In FIG. 4, a compass grinder guide 30 is shown having a tapered pin 32 at one end of the compass grinder guide for engaging the hole 26 on the top of the tooth. A radially extending bar portion 34 interconnects the pin 32 with an annular drill bit holder 36 having a hollow portion 38 for receipt of a drill bit.

A drill bit 40 has one end 42 mechanically anchored by a snap connection in a drill head 45. The drill head 45 is connected to a drive shaft 46 which extends through a handle portion 48 of a dentist drill. The shaft 46 and drill head 45 impart high speed rotational force to drill bit 40.

The drill head 45 may be air or battery driven. Alternatively the drill head and the shaft are removable from the handle portion 48 so as to limit the portion of the instrument that would need to be sterilized between different patients.

An internal lubrication system may be used to minimize drag on the drive mechanism of the drill bit. An edible oil, such as peanut oil, may be used to lubricate parts of the drill as necessary.

At the opposite end 44 of the drill bit 40 is located a tapered drill portion 46. The angle of taper and length of the drill portion 46 is varied depending upon the inclination and depth desired for the tooth prepared to receive a crown.

Figure 4A:
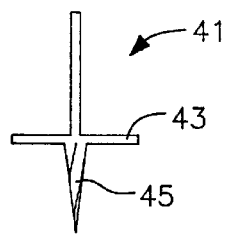
FIG. 4A is an alternate embodiment of a drill bit.

In FIG. 4A, an alternate drill bit 41 is shown. In this drill bit, a radially extending plate 43 located above the drill portion 45 provides a limit or stop to the depth of drilling possible by the drill portion 45. The plate 43 will engage the top of the prepared tooth to prevent further downward drilling.

Figure 4B:
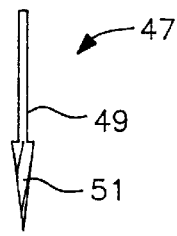
FIG. 4B is another alternate embodiment of a drill bit.

In FIG. 4B, drill bit 47 includes a narrowed diameter shank 49 as compared to larger diameter drill portion 51. The shank 49 visually alerts the dentist to desist from further drilling due to having reached a predetermined depth as measured by the height of drill portion 51.

Figure 5:
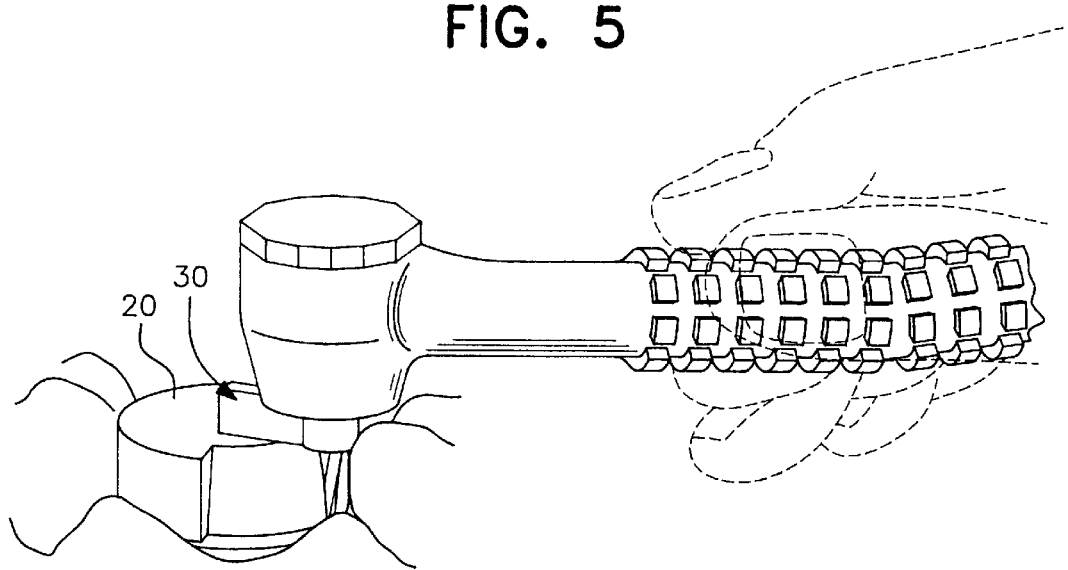
FIG. 5 illustrates the use of the compass grinder of the present invention to impart a predetermined angle of taper to a side wall of a prepared tooth.
Figure 6:
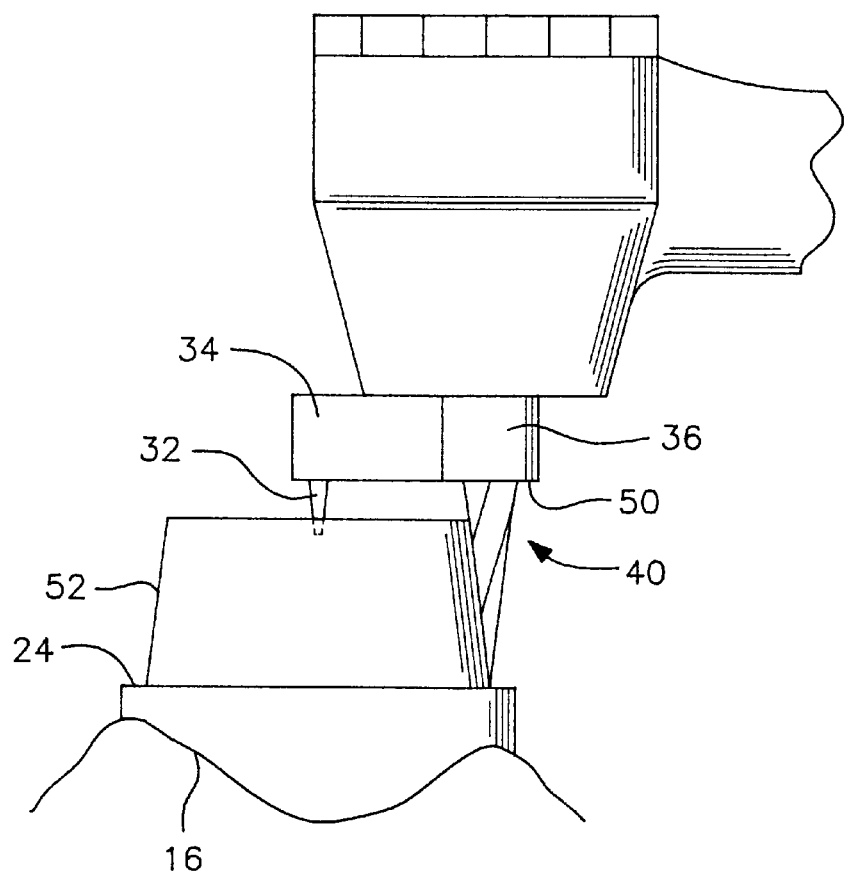
FIG. 6 is a side view illustrating application of a predetermined angle to a predetermined depth into a cylindrically formed upper portion of a tooth.

As shown in FIGS. 5 and 6, the compass grinder guide 30 is anchored in the upper surface 20 of a prepared tooth after removal of the pattern disk 22. The pin 32 engages in the hole 26 of the upper surface of the tooth. The drill bit 40 extends through the hollow portion of the bit holder 36. The drill bit 40 is set into the bit holder 36 to a predetermined depth so that the drill bit 46 will project from below a bottom surface 50 of the bit holder 36 to a predetermined depth.

Figure 7:
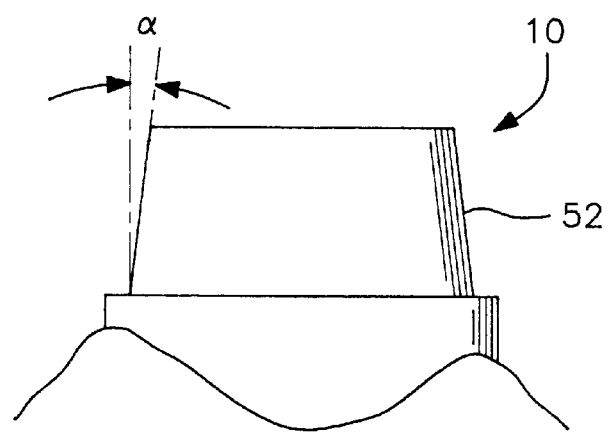
FIG. 7 is a side view illustrating the predetermined angle imparted to an upper portion of a prepared tooth.

By anchoring the pin 32 in the hole 26 and rotating the drill handle about the hole 26, using the hole 26 as a central axis, the grinding away of the tooth, as shown in FIG. 5, produces a truncated cone portion 52 as shown in FIGS. 6 and 7. Depending upon the angle of taper of the drill bit 46, the angle α, preferably between 1 and 10°, and more preferably between 3 and 8°, as shown in FIG. 7, will be varied to impart a predetermined taper to the upper portion of the tooth being prepared to receive a crown.

Simultaneously with and in preparation of securing a crown to a tooth, a crown is prepared by a lab technician having an internal recess of a predetermined base diameter, a predetermined depth and a predetermined diameter at the uppermost portion of the recess of the crown. The internal recess of the crown will exactly fit on the truncated conical portion 52 of the tooth 10 simultaneously prepared by the dentist, as shown in FIG. 7.

Figure 8:
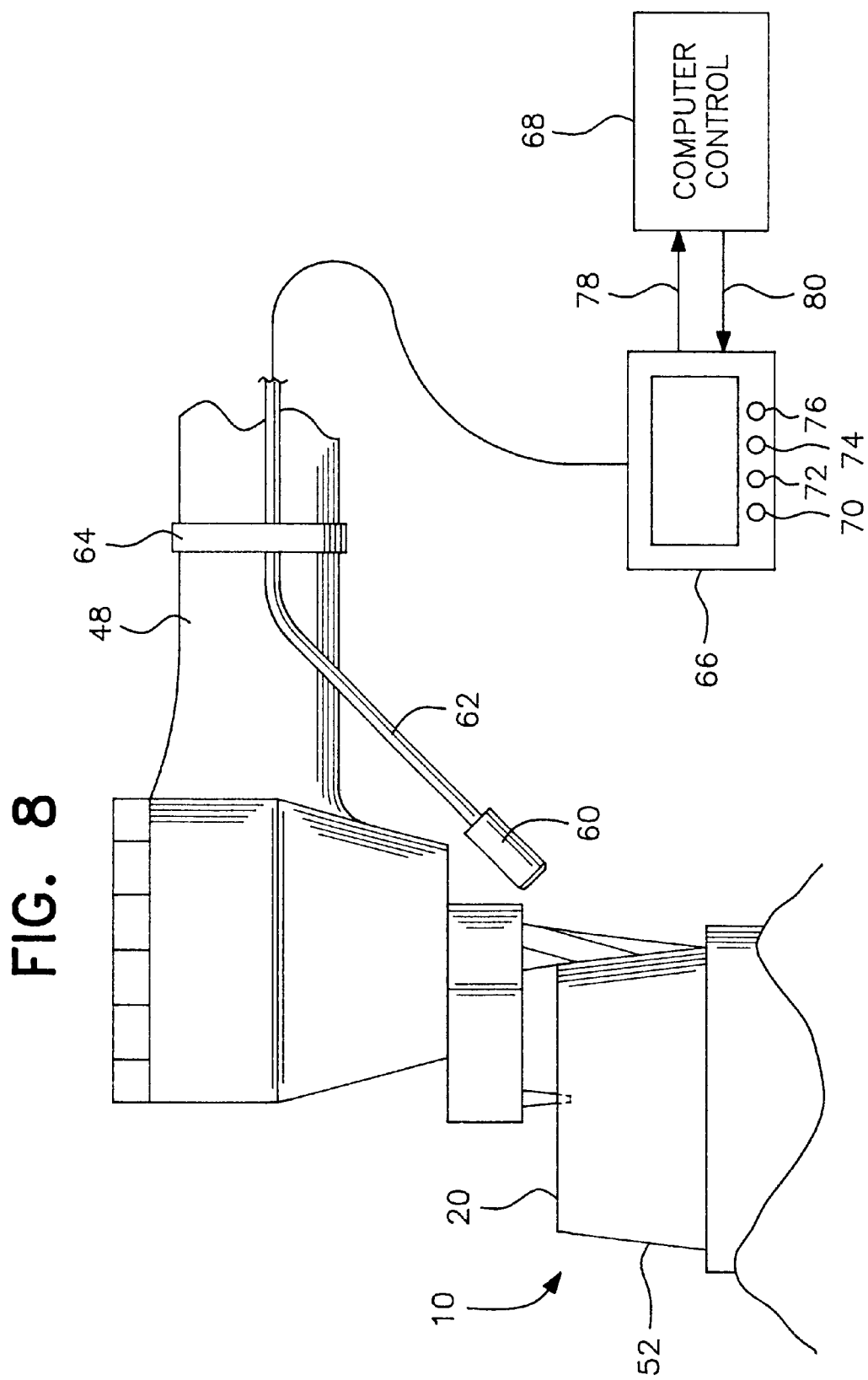
FIG. 8 illustrates the process of monitoring the drilling process and alerting a dentist to the correctness of the desired depth and angle of removal of tooth material.

As shown in FIG. 8, the grinding of the tooth 10 may be monitored by a television camera 60 having an optic fiber cable 62 secured to the handle 48 of the drill by a band 64. The cable transmits an image of the grinding operation to a monitor 66 and a computer controller 68 by line 78. The computer controller 68 activates a series of four lights 70, 72, 74 and 76 by line 80 depending upon the accuracy of the procedure being performed.

For example, a green light 70 would be activated to indicate that the compass grinder is positioned parallel to the upper surface 20 of the tooth. A blue light 72 would indicate that a desired depth or inclination is being achieved by the drill bit as also limited by the length of the burr. Alternatively, different sized burrs can be used to change the depth of penetration into the tooth. A red light 74 would warn that the drill bit is tilted creating an undercut whereas a yellow light 76 would indicate that an outward tilting of the drill bit is occurring to create an increased diameter portion of the truncated conical portion 52 or that the desired cutting depth is close to being achieved.

These lights as controlled by controller 68 will ensure an accurate mating of the prepared tooth with the simultaneously prepared crown which is made on the basis of an impression of the original tooth configuration as shown in FIG. 1. Based upon the knowledge that the upper surface of the prepared tooth will be flat at the deepest groove of its original surface and that a predetermined drill bit will be used to introduce a predetermined angular inclination of a tapered conical portion, to a predetermined depth, a crown can be prepared so that the crown may be secured to the tooth at the time of preparation of the tooth without a need for a subsequent office visit by the patient.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A method of preparing and securing a crown for a tooth, said method comprising the following steps, in order:
    taking an impression of a tooth in need of a crown,
    preparing an exterior surface of a crown based upon the impression of the tooth,
    preparing an internal recess of the crown, and
    preparing the tooth after preparing of the crown, so that an exterior configuration of the tooth matches the internal recess of the crown.

2. A method of preparing and securing a crown for a tooth as claimed in claim 1, wherein the tooth is prepared using a television camera, television monitor and a computer controlled guidance system to alert a dentist to any deviation from predetermined dimensions of the internal recess of the crown.

3. A method of preparing and securing a crown for a tooth as claimed in claim 2, wherein a series of lights are actuated by the computer controlled guidance system to help guide the dentist to properly prepare the tooth.

4. A method of preparing and securing a crown for a tooth as claimed in claim 1, wherein the tooth is prepared by grinding an uppermost surface flat, drilling a hole in the flat surface, anchoring a compass grinder in the hole, and rotating a drill bit in the compass grinder about an axis extending through the hole.

5. A method of preparing and securing a crown for a tooth as claimed in claim 4, wherein the compass grinder includes an annular drill holding portion for receiving the drill bit and for limiting depth of penetration of the drill bit.

6. A method of preparing and securing a crown for a tooth as claimed in claim 4, wherein a circular disk is placed on the uppermost flat surface for guiding removal of tooth material.

7. An apparatus for preparing a tooth for receipt of a crown, said apparatus comprising:
    a drive mechanism,
    a drill handle,
    a compass grinder having two ends spaced apart and interconnected by an elongated portion, one end of said two ends for rotatably mounting on a tooth, and
    a drill bit for mounting in the other of said two ends and said drill bit being driven by the drive mechanism and rotating in said other end of the compass grinder with said other end of said compass grinder rotating about said one end of said compass grinder for removing tooth material to prepare a tooth in a shape of a truncated cone.

8. An apparatus for preparing a tooth for receipt of a crown as claimed in claim 7, wherein said compass grinder includes a pivot pin at one end and an annular drill bit holder at an opposite end.

9. An apparatus for preparing a tooth for receipt of a crown as claimed in claim 7, wherein a television camera is mounted on the drill handle.

10. An apparatus for preparing a tooth for receipt of a crown as claimed in claim 9, wherein the television camera generates signals fed to a display monitor and a computer controller system.

11. An apparatus for preparing a tooth for receipt of a crown as claimed in claim 10, wherein said computer controller system actuates a series of lights based upon orientation of the drill bit.

12. An apparatus for preparing a tooth for receipt of a crown as claimed in claim 7, wherein the drill bit extends to a predetermined extent from said drill handle through said compass grinder.

13. An apparatus for preparing a tooth for receipt of a crown as claimed in claim 12, wherein the drill bit includes an angle cutting surface.

14. A system for preparing a tooth and securing a crown to the tooth, said system comprising:
    a drill handle,
    a drive mechanism in the drill handle,
    a drill bit mounted in the drive mechanism, and
    a compass grinder having two ends spaced apart and interconnected by an elongated portion, one end of said two ends for rotatably mounting on a tooth to be prepared for receipt of a crown, said drill bit extending through the other of said two ends of said compass grinder to a predetermined depth with said other end of said compass grinder rotating about said one end of said compass grinder and said drill bit having a cutting surface extending at a predetermined angle to remove tooth material in a shape of a truncated cone.

15. A system for preparing a tooth for receipt of a crown as claimed in claim 14, wherein a television camera is mounted on the drill handle.

16. A system for preparing a tooth for receipt of a crown as claimed in claim 15, wherein the television camera generates signals fed to a display monitor and a computer controller system.

17. A system for preparing a tooth for receipt of a crown as claimed in claim 14, further comprising a pre-formed crown having a predetermined internal recess for securing to the tooth immediately after the tooth material has been removed.

18. A system for preparing a tooth for receipt of a crown as claimed in claim 17, wherein the pre-formed crown is one of a plurality of pre-formed crowns having a choice of color and configuration.

19. An apparatus for preparing a tooth for receipt of a crown, said apparatus comprising:

a drive mechanism, a drill handle, a compass grinder, and a drill bit driven by the drive mechanism and rotating in the compass grinder for removing tooth material to prepare a tooth in a shape of a truncated cone, said compass grinder including a pivot pin at one end and an annular drill bit holder at an opposite end.

20. An apparatus for preparing a tooth for receipt of a crown, said apparatus comprising:

a drive mechanism, a drill handle, a compass grinder, a drill bit driven by the drive mechanism and rotating in the compass grinder for removing tooth material to prepare a tooth in a shape of a truncated cone, and a television camera mounted on the drill handle.

21. An apparatus for preparing a tooth for receipt of a crown as claimed in claim 20, wherein the television camera generates signals fed to a display monitor and a computer controller system.

22. An apparatus for preparing a tooth for receipt of a crown as claimed in claim 21, wherein said computer controller system actuates a series of lights based upon orientation of the drill bit.

23. A system for preparing a tooth and securing a crown to the tooth, said system comprising:

a drill handle, a drive mechanism in the drill handle, a drill bit mounted in the drive mechanism, a compass grinder pivotally mounted on a tooth to be prepared for receipt of a crown, and said drill bit extending through said compass grinder to a predetermined depth and having a cutting surface extending at a predetermined angle to remove tooth material in a shape of a truncated cone, a television camera mounted on the drill handle.

24. A system for preparing a tooth for receipt of a crown as claimed in claim 23, wherein the television camera generates signals fed to a display monitor and a computer controller system.

* * * * *